United States Patent [19]

Loffet

[11] 4,077,951

[45] Mar. 7, 1978

[54] L-PYROGLUTAMYL-L-PROLINAMIDE

[75] Inventor: Albert Loffet, Braine-le-Chateau, Belgium

[73] Assignee: U C B Societe Anonyme, Brussels, Belgium

[21] Appl. No.: 703,299

[22] Filed: Jul. 7, 1976

[30] Foreign Application Priority Data

Jul. 8, 1975 United Kingdom ............... 28678/75

[51] Int. Cl.$^2$ ......................................... C07C 103/52
[52] U.S. Cl. ......................... 260/112.5 R; 260/326.25
[58] Field of Search ............. 260/112.5 R, 112.5 TR, 260/326.25; 424/177

[56] References Cited

U.S. PATENT DOCUMENTS

| 3,135,748 | 6/1964 | Sheehan | 260/112.5 R |
| 3,309,353 | 3/1967 | Boissonnas et al. | 260/112.5 R |

OTHER PUBLICATIONS

Experientia 18, pp. 58–61 (1962).
J. Amer. Chem. Soc. (1955), pp. 1067–1068 vol. 77.

*Primary Examiner*—Delbert R. Phillips
*Attorney, Agent, or Firm*—Wenderoth, Lind & Ponack

[57] ABSTRACT

L-pyroglutamyl-L-prolinamide is useful for correcting metabolic or endocrinal disorders connected with senescence. It can be prepared by reacting L-pyroglutamic acid with L-prolinamide.

2 Claims, No Drawings

L-PYROGLUTAMYL-L-PROLINAMIDE

The present invention relates to a new compound, L-pyroglutamyl-L-prolinamide, to a process for preparing the same and to its therapeutic use in the treatment of senescence with a view to improving senile deficiencies.

According to the present invention, the new compound L-pyroglutamyl-L-prolinamide can be prepared by reacting L-pyroglutamic acid with L-prolinamide in the presence of a coupling reactant, in accordance with the following equation:

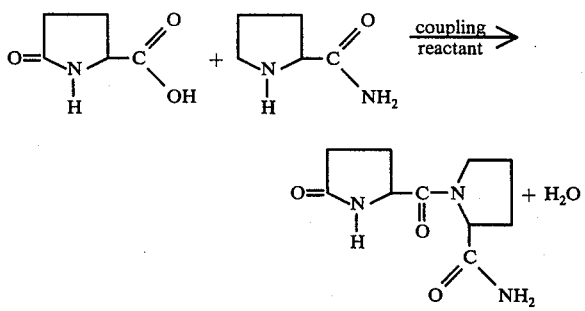

The two starting materials used for preparing L-pyroglutamyl-L-prolinamide are known and available commercially. Thus, L-pyroglutamic acid is marketed by Aldrich Chemical Co. Inc., while L-prolinamide is marketed by Cyclo Chemical. This latter substance can also be prepared by ammonolysis of the corresponding ethyl ester (see R. W. Chambers and F. M. Carpenter, J. Am. chem. Soc. 77, (1955), 1522–26.

Conventional coupling agents, particularly dicyclohexylcarbodiimide and 1-ethoxycarbonyl-2-ethoxy-1,2-dihydroquinoline can be used as coupling reactants for this reaction. With regard to the substances which can be used for this purpose, mention may be made of those enumerated in the review by Y. S. Klausner and M. Bodansky, published in Synthesis, 1972, pp. 453–463.

An organic solvent, such as tetrahydrofuran, dimethylformamide, dioxane, ethyl acetate, dichloromethane or the like, can be used as the reaction medium for the process of the present invention.

The following Example is given for the purpose of illustrating the present invention.

EXAMPLE 283.8 g. (1.2 mole) of L-pyroglutamic acid 193.1 g. (1.7 mole) of L-prolinamide are first introduced into a 10-liter three-necked flask provided with an agitator and a dropping funnel.

4 liters of dimethylformamide are then added, the resulting solution is cooled to 0° C. and, while stirring, 488 g. (2.37 moles) of dicyclohexylcarbodiimide, dissolved in 2 liters of dichloromethane, are added over the course of one hour. During the addition, the temperature is kept between 0° and 5° C. Stirring is continued for 48 hours, while gradually allowing the mixture to warm up to ambient temperature. 3 liters of water are then added to precipitate the dicyclohexylurea formed from the dicyclohexylcarbodiimide. The precipitate is filtered off and washed with water. The filtrate is evaporated to dryness and the residue taken up in 1 liter of water. A precipitate is formed and is removed by filtration. After evaporating the water, the oily residue obtained is dissolved in 1 liter of hot acetonitrile and the limpid solution thus obtained is allowed to crystallize in a refrigerator. The crystals obtained in this manner and filtered off, washed with 100 ml. of acetonitrile and dried.

A first batch of 262.6 g. of L-pyroglutamyl-L-prolinamide is thus obtained in a yield of 63.5%, referred to the starting prolinamide. Another batch of product can be recovered from the mother liquors, thus enabling the yield to be raised to about 70% of theory.

L-pyroglutamyl-L-prolinamide crystallizes in the form of a monohydrate; M.P. = 98° C; $[\alpha]_D^{22} = -100°$.

Elementary analysis: Calculated: C, 49.4%; H, 7.0%; N, 17.28%; $H_2O$ 7.40%. Found: C, 50.0%; H, 7.1%; N, 17.10%; 6.74%.

Nuclear magnetic resonance spectrum recorded with a 60 MHz Perkins-Elmer apparatus and with $D_2O$/TMS

| ppm | multiplicity | integr. | attribution |
|---|---|---|---|
| 2.1 | M | 4H | $2H^4$ $2H^3$ |
| 2.5 | M | 4H | $2H^\beta$ $2H^\gamma$ |
| 3.7 | M | 2H | $2H^\delta$ |
| 4.5 | M | 2H | $H^5$ $H^\alpha$ |

The protons of the amide groups of the L-pyroglutamic acid and of the L-prolinamide undergo exchange with $D_2O$ and therefore appear at $\delta = 4.65$ ppm.

The resonances have been attributed by comparison with the resonance spectra of the pyroglutamyl and prolinamide residues in the molecule of TRH (Tyrosine Releasing Hormone) (see S. Fermandjian et al., FEBS Letters, 28, (1972), 156 and J. C. Boilet et al., C.R. Acad. Sci. Paris, Series C 276, (1973), 217–220.

Analysis of the acid hydrolysate of the molecule indicates the correct stoichiometry for the different constituents: Glu/Pro/$NH_3$: 1/1/1.

PHARMACOLOGICAL PROPERTIES

It is known that, as the result of ageing, old people apparently not suffering from any well-defined illness are found to have a progressive series of more or less rapid involutional processes which appear as disturbances in the general homeostasis.

These deteriorations are frequent and appear mainly at the level of three endocrinal axes: the insulin axis, the thyroid axis and the gonad axis.

It is, for example, well known that the insulin response to alimentary or provoked hyperglycaemia is different and considerably reduced in the old man in relation to the response found in the healthy adult (pre-diabetes). The same is true of the iodine fixation capacity of the thyroid gland (see Handbook of Endocrinology, ed. R. D. Dillon, Lea and Febiger, Philadelphia, 1973).

At present, no therapy exists which enables these types of deteriorations to be effectively combated.

We have now found that the new compound of the present invention, L-pyroglutamyl-L-prolinamide, is useful for correcting metabolic or endocrinal disorders connected with senescence. This compound restores, in particular, the adaptability of the organism and its response to certain stimuli, for example induced hyperglycaemia, while not itself stimulating the release of insulin.

PHARMACOLOGICAL TESTS

1. Induced hyperglycaemia or glucose tolerance test (Dillon et al., loc. cit.)

The glucose tolerance test consists in administering orally to rats a dose of 1 g/kg glucose dissolved in 1 ml. of water and then measuring in the plasma the amount of insulin released (IRI) after 0, 15, 30, 60 and 120 minutes. The normal response to this test is a triangular figure in which the maximum insulin release is at about 15 minutes.

Ten 12 months' old rats are treated for one week with a physiological salt solution. On the last day, they are given an excess of glucose in accordance with the test described above. The insulin response is weak.

These same animals are then treated orally for 5 days with L-pyroglutamyl-L-prolinamide at a dose of 40 mg/kg, dissolved in 1 ml of water. The glucose tolerance test is then again carried out as before.

The results are indicated in the Table below:

| Measure at t = (minutes) | Insulinemias ($\mu$U/ml) | | | |
|---|---|---|---|---|
| | Before treatment | Extreme values* | After treatment | Extreme values* |
| 0 | 11 | 10.5–12 | 10.1 | 9.1–10.9 |
| 15 | 17 | 15.5–19 | 34 | 33.8–35 |
| 30 | 10.3 | 9.5–11 | 23 | 20.5–24 |
| 60 | 9 | 8.2–10.1 | 5 | 3.4–6.5 |
| 120 | 4.2 | 2.8–5.7 | 7.1 | 6 –8.6 |
| Surface of the triangular figure | 1100 | 978–1248 | 1541.2 | 1369.5–1697.25 |

*Extreme values: these values represent the extreme values measured on the same sample (the variations being due to the method of measuring used). They are not representative of any variation due to the animals themselves, the serum submitted to analysis being obtained by mixing the serums of the ten animals tested.

As a guide, a glucose tolerance test was realized on a group of young untreated rats. The results are indicated in the Table below:

| Measure at t = (minutes) | Insulinemias ($\mu$U/ml) | Extreme values |
|---|---|---|
| 0 | 8.5 | 7.5–9.5 |
| 15 | 21 | 20 –22.5 |
| 30 | 31 | 29 – 33 |
| 160 | 15 | 15 |

It should be observed that the insulin base rate before an excess of glucose is given (time 0), is not modified by the treatment. Therefore, this proves that the compound is not itself an insulin release agent.

Dogs were submitted to the same test. At the dose of 5 mg/kg the highest response to L-pyroglutamyl-L-prolinamide is obtained with dogs which have the highest base glycemias and insulinemias. Animals having low insulin rate but normal glycemia, give virtually no response to this treatment. At lower doses (1 mg/kg) the treatment had virtually no influence on the glucose and insulin rates, except for one pregnant female dog which showed high insulin rate and normal glycemia. After treatment, both glycemia and insulinemia were reduced to values exactly comparable with those of the other animals.

2. $^{14}$C GLUCOSE INCORPORATION TEST

During ageing, a general slowing down of cellular metabolism is observed i.e. both of energy producing systems (glycolysis, mitochondrial oxidations, etc.) and macromolecular biosynthesis systems (RNA and protein synthesis, etc.).

The purpose of this test is to follow the incorporation of $^{14}$C glucose in the macromolecular parts of aged animals. It was carried out on 10 20 months' old female NMRI mice having an average weight of 38 g $\pm$ 5 g.

After a 10 days treatment with L-pyroglutamyl-L-prolinamide (0.1 mmole/kg) and administration of a dose of $^{14}$C glucose, the animals were sacrified 5 hours later to determine the rate of $^{14}$C glucose incorporated in different organs (liver, heart, brain). The results show that incorporation of the radioactive precursor is stimulated at various degrees in the organic and proteinic extracts and in those fractions which are rich in RNA and DNA. Under the experimental conditions used, the most pronounced results are obtained in the brain (measured 5 hours after $^{14}$C glucose administration).

3. BEHAVIOR OF ANIMALS

During tests carried out on mice, it has been observed that the aged animals which had been treated with L-pyroglutamyl-L-prolinamide were more alert than the untreated ones. This increase in alertness could be worked out by putting in a cage an equal number of treated and untreated mice, then recording the order of capture of the animals. The interpretation was statistically made with the median test (W. J. CONOVER, Practical Non parametric Statistics, Wiley & Sons, 1971, p. 167). It has been observed that this difference in alertness between treated and untreated animals could only be found at the moment of the capture, their behavior at rest being identical.

Pharmaceutical preparations containing the new compound of the present invention can be administered intravenously, intraperitoneally, intramuscularly, subcutaneously and orally, for example in doses of from 1 to 200 mg/kg per day.

The following is an example of a pharmaceutical composition according to the present invention:

A No. 1 gelatine capsule contains:
25 mg of L-pyroglutamyl-L-prolinamide
400 mg of lactose and
10 mg of magnesium stearate.

I claim:
1. L-pyroglutamyl-L-prolinamide.
2. A pharmaceutical composition which comprises a therapeutically effective amount of L-pyroglutamyl-L-prolinamide and a pharmaceutical carrier.

* * * * *